Figure 1B:
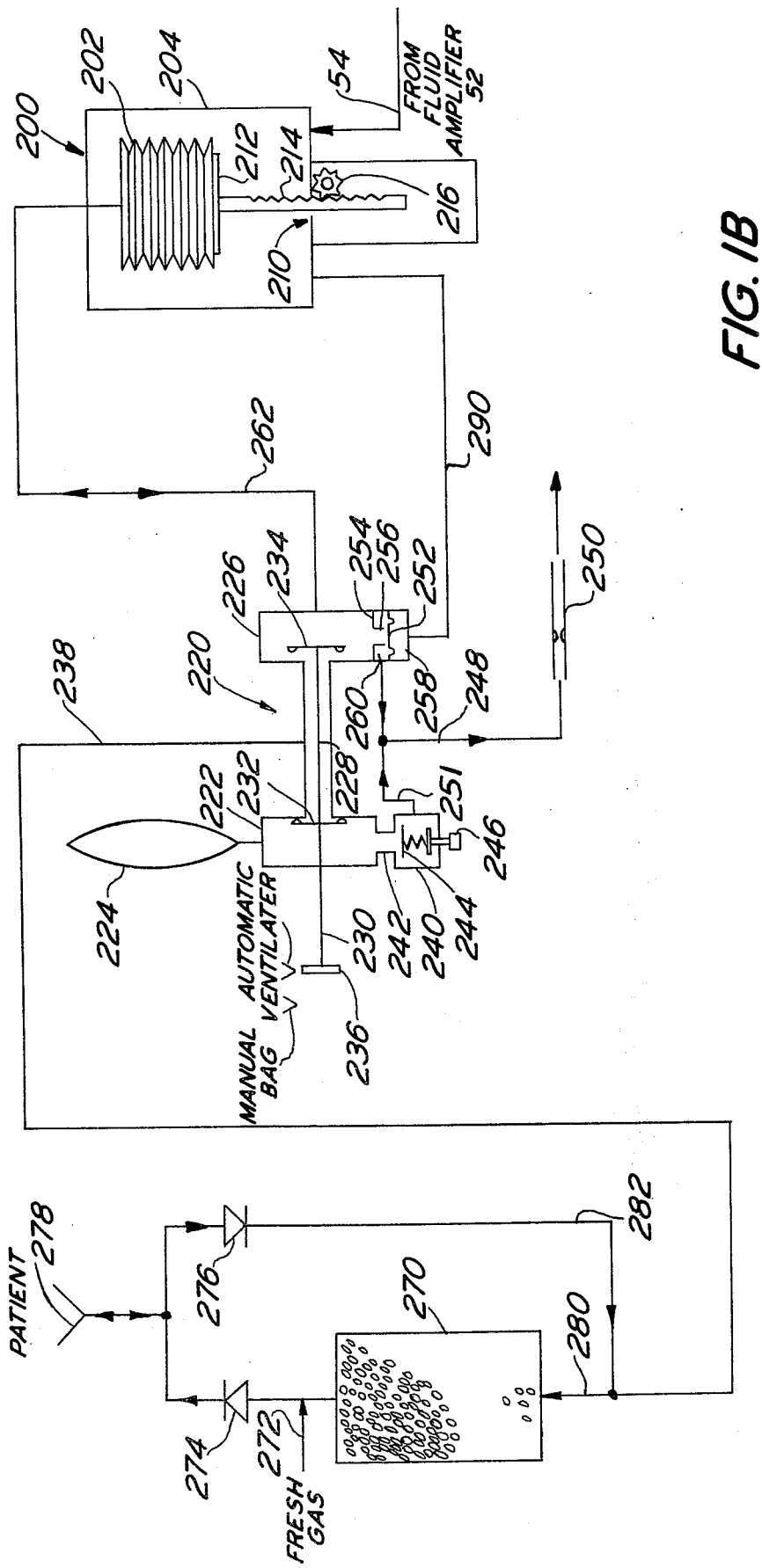

United States Patent [19]

Schreiber

[11] 4,007,736
[45] Feb. 15, 1977

[54] FLUIDIC CONTROLLED VENTILATOR

[75] Inventor: Peter J. Schreiber, Zionsville, Pa.

[73] Assignee: N.A.D., Inc., Telford, Pa.

[22] Filed: Mar. 12, 1975

[21] Appl. No.: 557,745

[52] U.S. Cl. .......................................... 128/145.8
[51] Int. Cl.$^2$ ...................................... A61M 16/00
[58] Field of Search ............... 128/145.5–145.8, 128/142–142.3, 146.5, 188, 203, 2.08, DIG. 17; 137/624.14, 835, DIG. 9

[56] References Cited

UNITED STATES PATENTS

| | | | |
|---|---|---|---|
| 2,121,311 | 6/1938 | Anderson et al. | 128/145.8 |
| 2,904,035 | 9/1959 | Andreasen | 128/145.8 |
| 3,537,450 | 11/1970 | Fox | 128/145.6 |
| 3,662,751 | 5/1972 | Barkalow et al. | 128/145.8 |
| 3,683,951 | 8/1972 | Beaumont | 128/145.8 |
| 3,730,180 | 5/1973 | Davison | 128/145.6 |
| 3,754,550 | 8/1973 | Kipling | 128/145.8 |
| 3,889,669 | 6/1975 | Weigl | 128/145.8 |

Primary Examiner—Robert W. Michell
Assistant Examiner—Henry J. Recla
Attorney, Agent, or Firm—Caeser, Rivise, Bernstein & Cohen, Ltd.

[57] ABSTRACT

A ventilator is disclosed having a power unit for driving the ventilator which includes fluidic timing control means, gas input means and gas output means. The gas input means is connected to the timing control means via pressure regulating means. Display means are provided to the timing control means. The timing control means is connected to the output means and is alternately conductive and non-conductive of gas from the input means to the output means. The ratio of the periods of conductivity to non-conductivity remain fixed even where the frequency of alternation varies to maintain a fixed ratio of the inspiratory to expiratory phase time.

12 Claims, 3 Drawing Figures

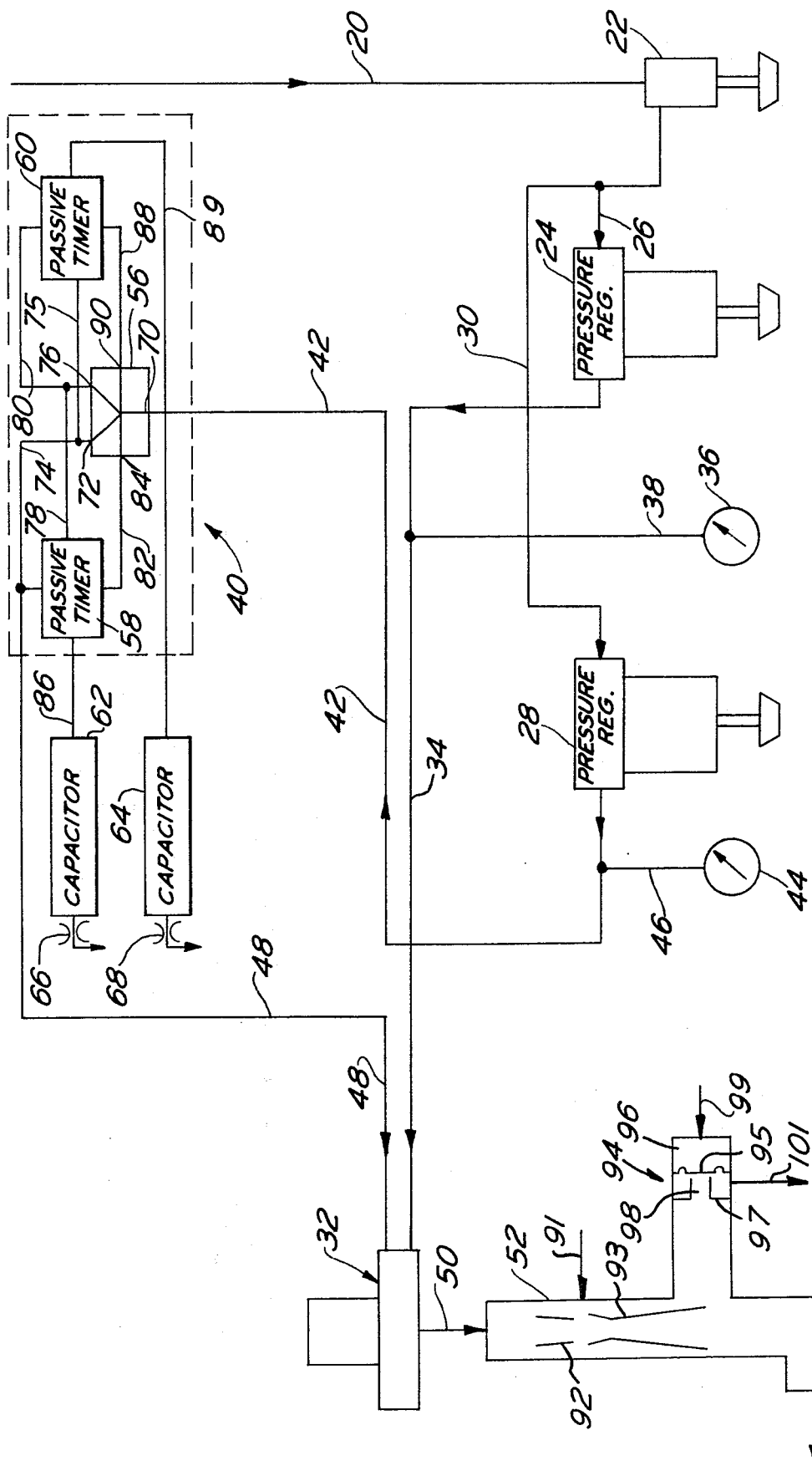
FIG. IA

FLUIDIC CONTROLLED VENTILATOR

This invention relates generally to ventilators and more particularly to a fluidic power unit for an anesthesia ventilator.

Lung ventilators are well known for use in the artificial ventilation of the lungs. These ventilators, by means of presetting of certain respiratory parameters, inflate and deflate the lungs of a patient connected to the lung ventilator. Among the respiratory parameters which must be preset are the values for tidal volume, respiratory minute volume, respiratory frequency, inspiratory phase time, inspiratory/expiratory phase time ratio, inspiratory flow, inspiratory pressure, and others. Unfortunately, all of these parameters are interrelated and therefore adjustment of one of the parameters normally causes a change of one or more of the other parameters. However, it is normally preferred that changing the presetting of one parameter does not require the readjustment of the settings for other of the parameters. A preferred ventilator control combination would thus consist of controls for respiratory frequency, tidal volume and inspiratory flow, which would have a fixed ratio of inspiratory to expiratory phase time through a range of frequency settings. A display of the respiratory frequencies would also be most advantageous.

Prior systems which have had the capability of changing the frequency while having a fixed ratio of inspiratory to exspiratory phase time and a display of the respiratory frequency rate have been unduly expensive. The inexpensive systems have required constant readjustment of other settings in order to maintain a fixed ratio of inspiratory to expiratory phase time where the frequency setting has been changed.

It is therefore an object of the invention to overcome the aforementioned disadvantages of the prior art.

Another object of this invention is to provide a new and improved ventilator control combination which includes controls for respiratory frequency having a fixed ratio of inspiratory to expiratory phase time.

Still another object of this invention is to produce a power unit for a lung ventilator having a control circuit with direct control for respiratory frequency with visual display thereof.

Yet another object of this invention is to provide a new and improved fluidic controlled anesthesia ventilator system.

Still another object of this invention is to provide a new and improved power unit for a ventilator which utilizes a fluidic timing control which oscillates at a plurality of frequencies while maintaining a fixed ratio of inspiratory to expiratory phase time.

Another object of the invention is to provide a new and improved power unit for a ventilator which includes fluidic timing control means, gas input means and gas output means. The gas input means is connected to the timing control means via pressure regulating means and display means are provided responsive to the pressure of the gas provided to the timing control means. The timing control means is connected to the output means and is alternately conductive and non-conductive of gas from the input means to the output means. The ratio of the periods of conductivity to non-conductivity remain fixed.

These and other objects of the invention are achieved by providing a power unit for a ventilator which has a fluid operated timing control. The timing control has input means connected to a fluid source via means for varying the input pressure of the fluid to the timing control and display means responsive to the input pressure. The timing control is changeable in state for controlling the period of inspiratory time and expiratory time. The frequency of the timing control means is controllable in response to the input pressure so that respiratory frequency can be controlled and monitored by varying the input pressure and viewing the display means.

Figure 2:
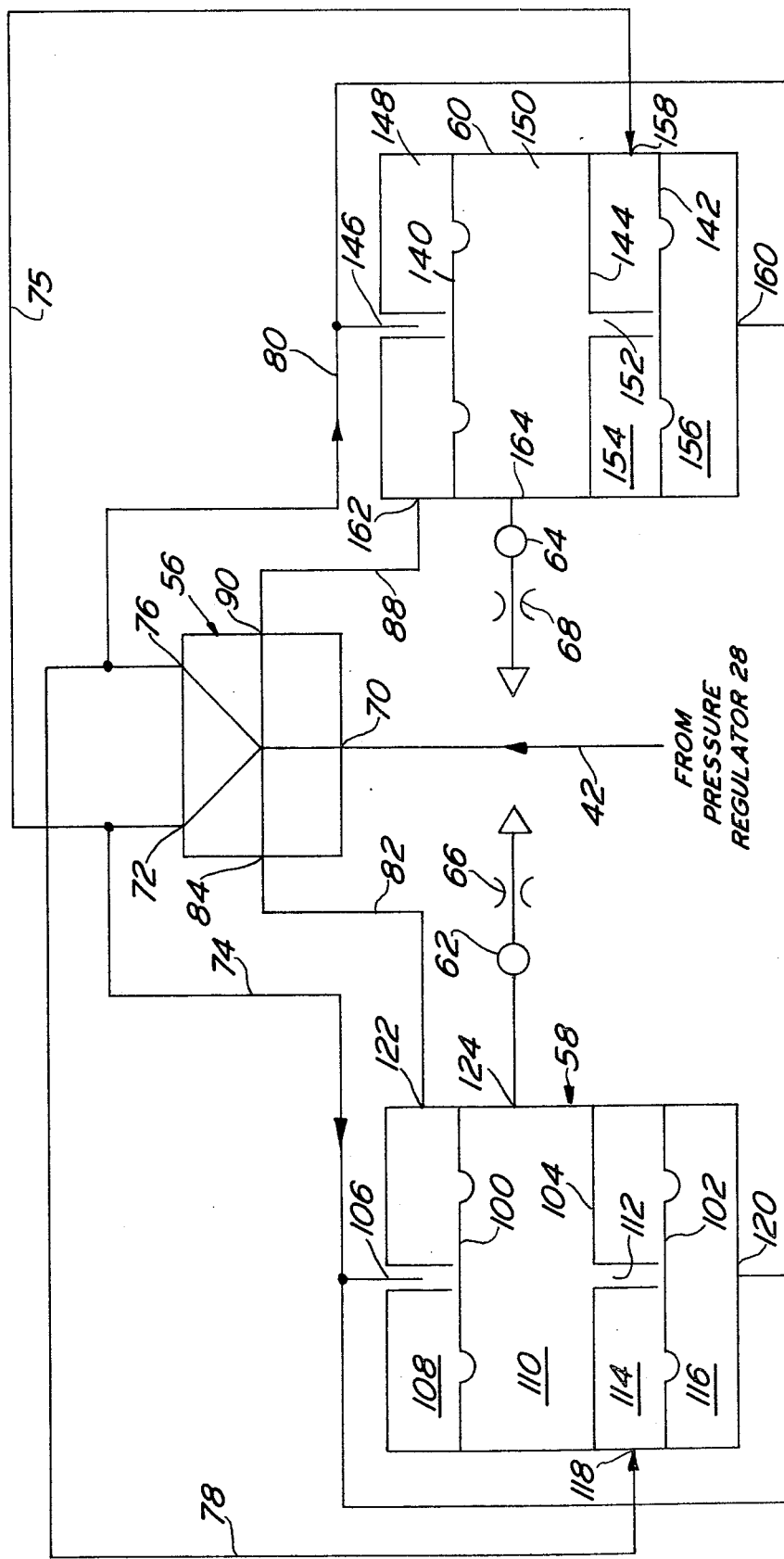

Other objects and many of the attendant advantages of this invention will be readily appreciated as the same becomes better understood by reference to the following detailed description when considered in connection with the accompanying drawing wherein:

FIG. 1 is a schematic block diagram of a fluidic controlled anesthesia ventilator comprised of FIGS. 1A and 1B; and FIG. 2 is a schematic block diagram of the oscillator used in the timing control unit.

Referring now in greater detail to the various figures of the drawing wherein like reference numerals refer to like parts, a fluidic controlled ventilator is shown generally in FIGS. 1A and 1B.

The ventilator shown in FIG. 1A includes a fluid input line 20 which is connected via an ON/OFF valve 22 to a pressure regulator 24 via line 26 and to pressure regulator 28 via line 30. The output of pressure regulator 24 is connected to a pressure controlled ON/OFF valve 32 via line 34. A pressure gauge 36 is connected to line 34 via line 38. The output of pressure regulator 28 is connected to a timing control unit 40 via line 42. A pressure gauge 44 is connected via line 46 to line 42. The output of timing control unit 40 is connected to the pressure controlled ON/OFF valve 32 via line 48 to control the opening and closing of the valve 32. The output of pressure controlled ON/OFF valve 32 is connected via line 50 to a fluid injector 52. The output of fluid injector 52 is connected via line 54 either to an anesthesia ventilator which includes indirect power transmission or directly to a patient for breathing purposes.

The timing control unit 40 includes a fluidic flip flop 56, a pair of passive timers 58 and 60, and a pair of capacitors 62 and 64, the outputs of which are connected to bleed orifices 66 and 68, respectively.

Line 42, which is the output of pressure regulator 28, is connected to the supply port 70 of flip flop 56. The output port 72 of flip flop 56 is connected via line 74 to the passive timer 58 and to output line 48 of the timing control unit 40, which is in turn connected to the pressure actuated ON/OFF valve 32 and via line 75 to passive timer 60. Output 76 of flip flop 56 is connected to passive timer 58 via line 78 and to passive timer 60 via line 80. The passive timer 58 is connected via output line 82 to the control input 84 of flip flop 56 and to capacitor 62 via line 86. The passive timer 60 is connected via line 88 to the control input 90 of flip flop 56 and to capacitor 64 via line 89.

The capacitor 62 is connected to bleed orifice 66 and capacitor 64 is connected to bleed orifice 68. The flow capacity of orifices 66 and 68 have a ratio of 2 to 1 (2/1), respectively, in order to provide a preferred inspiratory-expiratory phase time ratio of 1 to 2 (½). Other fixed ratios may also be used by varying the flow capacities of the bleed orifices. The volume of the capacitors 62 and 64 are preferably adjustable as to the volume of the capacitors to enable fine adjustment of the phase time ratio of the oscillation of the flip flop 56 when pressure is applied via line 42 to the input thereof. The volume of capacitors 62 and 64 may also be fixed.

The operation of the timing control unit is best understood with respect to FIG. 2. As seen in FIG. 2, each of the passive timers 58 and 60 are each fixed volume chambers having a similar construction and each of which includes four chambers which are defined by a pair of diaphragms and an inner wall.

The passive timer 58 includes a first diaphragm 100, a second diaphragm 102 and a wall 104. The timer also includes an inlet port 106 which is closeable by diaphragm 100 when diaphragm 100 is urged against the inner end or lip of port 106. The diaphragm 100, in combination with an end wall of passive timer 58, defines chamber 108. The main chamber 110 of the passive timer 58 is the portion of the passive timer between the diaphragm 100 and wall 104. Wall 104 includes a port 112 which is engageable by diaphragm 102 and is closed thereby when so engaged. The wall 104 and diaphragm 102 define a chamber 114 therebetween and the diaphragm 102 and the end of passive timer 58 define a chamber 116 therebetween. The passive timer 58 also includes a pair of inlet ports 118 and 120. Port 118 connects output line 78 from flip flop 56 to chamber 114 of the passive timer 58 and port 120 connects output line 74 of flip flop 56 to chamber 116 of passive timer 58. Passive timer 58 includes an outlet port 122 which is connected via line 82 to control port 84 of flip flop 56. An outlet port is also provided from chamber 110 of passive timer 58 and this port 124 is connected to the capacitor 62 which is in turn connected to the bleed orifice 66. Passive timer 60 is of like construction to passive timer 58 and includes diaphragm 140, diaphragm 142, wall 144, port 146, chamber 148, chamber 150, port 152, chamber 154, chamber 156, inlet port 158, inlet port 160 and outlet ports 162 and 164.

Port 146 is engageable by diaphragm 140 which, when so engaged, closes port 146. Port 152 is closeable by diaphragm 142 when engaged thereby. Chamber 148 is defined between one end wall of passive timer 60 and diaphragm 140. Chamber 150 is defined between diaphragm 140 and wall 144, chamber 154 is defined between wall 144 and diaphragm 142 and chamber 156 is defined between diaphragm 142 and the other end wall of the passive timer 60.

The flip flop 56 is a conventional wall attachment amplifier which receives a flow of fluid at a supply port 70 and has an output at port 72 or 76 in accordance with the pressure applied to the control ports 84 and 90. When pressure is applied at control port 84, the supply fluid provided at port 70 is deflected to outlet port 76. Similarly, when the pressure is greater at control port 90 than at control port 84, the fluid provided to supply port 70 is deflected to outlet port 72.

The flip flop 56 is connected, in combination with the timing chambers, capacitors and bleed orifices, as a bistable multivibrator which oscillates at a frequency in accordance with the pressure provided in line 42 from pressure regulator 28.

The object of the circuit is that it be able to oscillate at a fixed rate for a specific pressure. As the pressure increases at the supply port 70, the frequency of oscillation is decreased and similarly when the pressure at the supply port 70 is reduced, the rate of oscillation is increased.

The flow capacity of the bleed orifices 66 and 68 are approximately 2 to 1 (2/1) which provides a phase time ratio of the time that the fluid is directed to the outlet port 72 to the time that the fluid is directed to outlet port 76 of 1 to 2 (½) to enable an inspiratory to expiratory phase time ratio of 1 to 2 (½).

In operation, if it is assumed that the control pressure at a specific time is greater at port 90 than it is at port 84, fluid is directed from supply port 70 to outlet port 72 which thereby provides pressure to inlet ports 106 and 120 of passive timer 58. As soon as the pressure is provided to port 120, diaphragm 102 engages port 112 and thereby isolates the chamber 114 from chamber 110 of passive timer 58. In the prior phase of the cycle, when pressure was applied to chamber 110 from the outlet port 76 of flip flop 56 via line 78 and inlet port 118 and port 112, the chamber 110 reached a pressure whereby the diaphragm 100 was urged against inlet port 106. Accordingly, inlet port 106 remains closed until such time as the pressure in chamber 110 is reduced by the loss of fluid through the bleed orifice 66 and the diaphragm 100 is moved away from port 106.

The period of time it takes for the pressure in chamber 110 of the passive timer 58 to reduce sufficiently to enable the port 106 to be opened determines the portion of the oscillation cycle which controls the inspiratory phase time. As soon as the port 106 opens, the pressure provided in line 74 from port 72 of flip flop 56 is applied via port 122 and line 82 to the control input 84 of flip flop 56. As soon as the pressure is provided to input 84, the supply fluid is diverted to output port 76 of flip flop 56. As soon as the fluid pressure is provided to output port 76 of flip flop 56, pressure is provided via line 78 to chamber 114 of the passive timer 58 thereby causing the diaphragm 102 to be released from port 112 and thereby provide fluid communication to chamber 110 for building the pressure in chamber 110 which causes the diaphragm 100 to close port 106.

The output pressure from port 76 of flip flop 56 also causes the chamber 156 to be charged with pressure and thereby causes the diaphragm 142 to close port 152 of wall 144. This acts to isolate the chamber 150 of timer 60 from the pressure at output 72 of flip flop 56.

Port 146 remains closed until the pressure in chamber 150 is reduced by the loss of fluid through the bleed orifice 68 and the diaphragm 140 is moved away from the port 146.

As soon as the port 146 is opened, the pressure in chamber 148 is transmitted via line 88 to the control input 90 of flip flop 56, thereby causing the fluid flow to be diverted from output port 76 to output port 72. The increase of pressure at output port 72 is immediately transmitted via line 75 to chamber 154 causing the opening of port 152 and the charging of pressure into chamber 150 of passive timer 60.

It can therefore be seen that the flip flop 56 is changed from one state to another and thereby oscillates as a result of the feedback circuits formed of passive timers 58 and 60 and the associated capacitors and bleed orifices therewith.

It should also be noted that the flow of fluid out of orifices 66 and 68 determines the portion of the cycle that output port 72 is conductive of the supply fluid to flip flop 56. In view of the fact that the output port 72 controls the inspiratory phase time of the respiratory cycle, it is preferred that the ratio of the inspiratory phase time to expiratory phase time be 1 to 2 (½) and therefore the period in which the flow of fluid from supply port 70 be to output port 72 is preferably one-half of the time that the supply port supplies fluid to output port 76. Accordingly, the flow of fluid through bleed orifice 66 is approximately twice that of bleed orifice 68 so that the pressure in chamber 110 is reduced twice as fast as the pressure in chamber 150 to enable diaphragm 100 to be released from port 106 in one-half the time that it takes to release the diaphragm 140 from port 146.

Thus, the output pressure from port 72 of flip flop 56 on output line 48 via line 74 is high for approximately one-third of each oscillation of flip flop 56. The frequency of oscillation is controlled by the amount of pressure in line 42 from pressure regulator 28. As the pressure is increased, the oscillation rate is decreased because the increased pressure at supply port 70 causes the capacitors 62 and 64 to be changed to a greater pressure during each phase of the respiratory cycle. Therefore, it takes a greater period of time for the capacitors' pressure to be reduced via the bleed orifices 66 and 68. The longer the period to reduce the pressure in the capacitors 62 and 64, the longer the period to reduce the pressures in chambers 110 and 150 which are connected respectively thereto. Of course, as the pressure to port 70 is decreased, the oscillation rate increases.

The operation therefore of the overall ventilator control unit shown in FIG. 1A is as follows:

Gas, preferably oxygen or compressed air, is provided in line 20, which is transmitted to the ON/OFF valve 22. When the ON/OFF valve 22 is on, it conducts the gas in line 20 to the pressure regulator 24 and the pressure regulator 28. The output of pressure regulator 24 is provided via line 34 to the pressure operated valve 32. The pressure regulator 24 has a manual adjustment for regulating the pressure. The gauge 36 provides a visual display which is changeable in accordance with the pressure in line 34. The gauge is preferably calibrated in terms of inspiratory flow. The flow characteristics of the fluid injector 52 must be taken into consideration in order to accurately calibrate the pressure gauge 36 in terms of inspiratory flow.

The output of the pressure regulator 28, which is also manually variable, is fed via line 42 to the timing control 40. As set forth above, the timing control 40 acts to provide a two phase or bistable repetitive signal on output line 48 of the timing control. The pressure provided in line 42 from pressure regulator 28 is connected to gauge 44 which provides an output display in accordance with the pressure in line 42. After it is determined what the oscillatory rate of the timing control 40 is for each of the various pressures provided thereto in line 42, the gauge 44 is calibrated in accordance with the respiratory frequency. Each time the fluid pressure at supply port 70 is directed towards outlet port 72, the pressure on output line 48 of the timing control 40 goes high and thereby causes valve 32 to be opened to pass fluid in line 34 via valve 32 to output line 50.

The output line 50 is provided to fluid injector 52. The fluid injector 52 is of conventional construction and preferably includes a venturi mechanism which enables a mixture of the fluid provided from line 50 with fluid provided in port 91. The fluid in port 91 is preferably delivered either from the atmospheric air or another gas fluid.

The fluid injector 52 includes a first nozzle 92, a second nozzle 93 and a pressure relief valve 94. The port 91 is located adjacent the inner end of the first nozzle 92 to provide gas to the annular opening between the exit of the first nozzle 92 and the entrance port of the second nozzle 93.

Pressure relief valve 94 includes a diaphragm 95 which is provided at one end of a sealed chamber 96 and a wall 97 having a port 98. The line 50 is connected to chamber 96 via a pilot line 99.

The gas flow from the first nozzle 92 to the second nozzle 93 sucks atmospheric air or other gas supplied via line 91 into the second nozzle 93 to add to the gas supplied to line 54 when there is a flow of gas into line 50. The pressure in line 50 also causes the relief valve 94 to be closed as the increased pressure fills chamber 96 and thereby causes a closing of the relief valve 94 by having diaphragm 95 engage the lip of port 98. When the expiratory phase of the respiratory cycle starts, the pressure in line 50 is reduced thereby causing the diaphragm 95 to be removed from the lip of port 98 and thereby enabling gas to be expelled via port 98 to the atmosphere via line 101 to enable the expiratory phase of breathing.

The output line 54 is capable of delivering gas directly to the patient for breathing purposes or may be used as a power supply for a ventilator with indirect power transmission.

It can therefore be seen that a new and improved power unit for a ventilator has been provided. It should be noted that by regulating the pressure with valve 28, the frequency of oscillation can be changed which thereby changes the respiratory frequency of gas provided via line 50 and/or via line 54 where fluid amplification is necessary or is desired to mix oxygen with atmospheric air. Because the phase relationship of the repetitive cycle remains the same, irrespective of the frequency, the timing control 40 enables the pressure actuated valve 32 to open and close in a fixed phase ratio, irrespective of the oscillation rate of the timing control 40. Each time pressure is provided in line 48, the valve 32 is caused to open and thereby provide fluid for the inspiratory portion of the ventilation cycle and, when pressure is reduced in line 48, prevents the passage of a ventilating fluid to line 50 during the expiratory portion of the ventilation cycle.

Moreover, because the pressure gauge 44 and the display thereof is calibrated in terms of respiratory frequency, as the pressure regulator 28 is varied, the operator has instantaneous display of the respiratory frequency provided to the patient.

An anesthesia ventilator which is preferably controlled by the ventilator circuit shown in FIG. 1A, is shown in FIG. 1B. Line 54 from fluid injector 52 is connected to a ventilator of the type having an indirect power transmission. That is, the ventilator includes a volume control 200 having a bellows 202 which is provided in a closed container 204. Thus, the inspiratory pressure is not directly from line 54 to the patient, but rather comes from the bellows 202 as the pressure from line 54, which is connected to the container 204, fills the container 204 and thereby compresses the bellows 202. It should be noted that the volume control 200 includes an adjustment mechanism which can be manually varied for the purpose of determining the amount of gas provided to the patient during each inspiratory phase of each respiration cycle. The adjustment mechanism 210 thus includes a platform 212 which bears against one end of the bellows 202 to define the maximum amount of expansion of the bellows. Platform 212 is supported by an elongated leg 214 which includes a rack of teeth which are engageable by a pinion 216. The pinion 216 is manually rotatable for the purpose of adjusting the size of the bellows for the purpose of controlling tidal volume during the ventilation cycle.

The anesthesia ventilator further includes a switching mechanism 220 which enables operation of the anesthesia ventilator in either of two modes. The first mode is a manual mode whereby a bag is used for inspiration and expiration during the ventilation cycle and the second mode is the automatic ventilation mode from the volume control 200 and the automatic power and timing circuit shown in FIG. 1A.

The switching mechanism 220 includes a chamber 222, chamber 226 and a connecting line 228 which extends between chambers 222 and 226. The switching mechanism further includes a manually movable rod 230 to which is connected a pair of cover plates 232 and 234. A handle 236 is connected at one end of the rod and is preferably connected adjacent an indicating plate which preferably includes the legends illustrated to indicate whether the switching mechanism 220 is in a position to enable operation manually with bag 224 or by the automatic ventilator volume control 200.

The cover plate 232 is connected to the rod 230 centrally of the rod 230 with cover plate 234 being provided at the end of rod 230 opposite the end supporting handle 236. The cover plates are so disposed with respect to rod 230 that when rod 230 is at the innermost position with respect to the switching mechanism 220, the cover plate 232 covers the port between line 228 and chamber 222 to isolate fluid communication therebetween. This enables cover plate 234 to be removed from the port between line 228 and chamber 226 and thereby enables fluid communication from the ventilator volume control 200 to the patient via a line 238 which is connected to line 228.

When the rod 230 is in its outermost position with respect to the switching mechanism, the cover plate 234 covers the port joining line 228 to chamber 226, thereby isolating the ventilator volume control 200 from line 238 by causing fluid communication between bag 224 and line 238. At the bottom of chamber 222 there is provided a relief valve 240 which comprises a chamber connected via port 242 to chamber 222. The port is normally closed by plate 244 which is spring urged against port 242.

A manually actuable member 246 is provided for adjusting the pressure at which the port 242 can be opened and thus provides fluid communication between chamber 222 and the lower chamber 240. Chamber 240 has an outlet port which is connected to exhaust line 248 via line 251 which is in turn connected to a line 250 which is preferably directed toward the floor and leads to the atmosphere. Line 250 may also be connected to a hospital suction system, a non-recycling air conditioning system or a scavenger system. If line 250 is connected to a suction system, means must be provided to prevent subatmospheric pressure in the system.

Chamber 226 includes a diaphragm valve comprised of diaphragm 252, a wall 254 having a port 256. Diaphragm 252 closes port 256 by engaging the lip thereof when the pressure in chamber 258 is above a predetermined pressure. When the port 256 is open, there is fluid communication between chamber 226 and exhaust line 248 via port 260. Chamber 226 is also connected via line 262 to the interior of bellows 202.

The anesthesia system is a circle system which includes an absorber canister 270, a fresh gas port 272, an inspiratory valve 274, an expiratory valve 276 and an outlet port 278 for connection to a patient's lungs.

The line 238 is connected to the input line 280 of the absorber canister 270 and the output line 282 from the expiratory valve 276. The output port 278 is connected to the output line from the inspiratory valve 274 and connected to the input line to the expiratory valve 276.

It should be noted that in the anesthesia ventilator system shown in FIG. 1B, the fresh gas is delivered continuously into the system during the ventilation cycle. The relief valve, comprised of diaphragm 252 and port 256 of wall 254, during automatic ventilation, enables discharge of a volume of gas equal to the fresh gas delivered to the system and during manual ventilation the relief valve, including plate 244 and port 242, provides the same function.

In the automatic ventilator operation, when pressure is provided in line 54 to the ventilator volume control 200, the inspiratory phase is initiated by the pressure in container 204. That is, the diaphragm 252 is caused to close port 256 as pressure is provided to chamber 258 from the pressure in container 204 via line 290.

As the pressure in container 204 is increased and the flow of fluid therein continues, the bellows 202 is closed to its smallest volume thereby causing fluid to be driven through line 262 through chamber 226 and line 228 through line 238, through canister 270 and in turn through the inspiratory valve 274 to port 278. As soon as the pressure in line 54 is reduced, it causes the expiratory phase to start by causing the pressure in container 204 to be reduced below the pressure in the lungs of the patient and thereby causing a reverse flow of fluid to the interior of bellows 202. The pressure in chamber 226 is larger than the pressure in chamber 258 which causes port 256 to be opened to release excess gas during the expiratory phase. When port 256 is open, excess gas is expelled via line 250 from port 260 and port 256, from the fluid delivery system. Bellows 202 is expanded during the expiratory phase as the pressure in line 262 is increased and relief valve 94 of amplifier 52 is opened to permit gas in container 204 to be expelled via port 98 and line 101. The line 250 is isolated from chamber 226 as soon as the pressure in line 54 is again increased at the beginning of the inspiratory phase. The increased pressure in container 204 is transmitted to chamber 258 which causes the diaphragm 252 to close port 256. Ventilation during the inspiratory phase is then provided from the bellows 202 to the patient at port 278.

The process is of course repeated. In order to provide manual operation, the rod 230 is drawn to the outermost position adjacent the "Manual Bag" setting with the cover plate 234 covering the port between line 228 and chamber 226 and isolating the automatic ventilator from the patient. During the inspiratory phase the bag 224 is squeezed to force air through lines 238 via the absorber canister 270 and inspiratory valve 274 to the patient via port 278. Gas is then expelled from the patient's lungs and returns via line 228 to bag 224.

With rod 230 of switching mechanism 220 in the "Manual Bag" position, spontaneous breathing of the patient is enabled. That is, the patient, by inhaling and exhaling, causes gas to move between port 278 and bag 224. Accordingly, in the "Manual Bag" position of switching mechanism 220 both manually assisted and spontaneous breathing of a patient can be accomplished. During the manual cycle excess gas is expelled from the system via relief valve 240.

It should be noted that the fresh gas is delivered continuously into the system during the entire operation. The excess gas is discharged through the relief valves provided in chambers 222 and 226 when the pressure differential opens the valves.

Without further elaboration the foregoing will so fully illustrate my invention that others may, by applying current or future knowledge, readily adapt the same for use under various conditions of service.

What is claimed as the invention is:

1. A power unit for a ventilator having a fluid operated timing control, said timing control having input means connected to a fluid source via means for varying the input pressure of said fluid to said timing control, and display means including graduations calibrated to read respiratory frequency which is responsive to said input pressure, said timing control being changeable in state for controlling the period of inspiratory time and expiratory time, said timing control including means responsive to said input pressure for controlling the frequency of the change of state of said timing control in accordance with said input pressure so that respiratory frequency can be controlled and monitored by varying said input pressure and viewing said display means.

2. The power unit of claim 1 wherein said timing control includes an oscillator having a pneumatic timing circuit for varying the flow of gas to control the frequency of oscillation and the phase time ratio of the inspiratory to said expiratory time.

3. The power unit of claim 2 wherein said pneumatic timing circuit includes a pair of passive timers which include bleed orifices for bleeding off pressure from each of said timers whereby, the ratio of said orifices controls said phase time ratio.

4. The power unit of claim 3 wherein said passive timers are utilized in combination with a fluid flip flop having a supply port and a pair of outputs with each of said passive timers being connected to both of the outputs of said flip flop for controlling the amount of time that each of said outputs of said flip flop are conductive of fluid from the supply port thereof.

5. The power unit of claim 4 wherein means for connecting each of the passive timers to one of the control inputs of said flip flop is provided for deflecting the flow of fluid from said supply port of said flip flop to the other of said orifices after a predetermined portion of the oscillation cycle of said flip flop.

6. The power unit of claim 5 and further including a pressure responsive ON/OFF valve and means for connecting one of said outputs of said flip flop to said pressure responsive ON/OFF valve, said ON/OFF valve also having connected thereto a supply of gas for passage to a patient, said pressure responsive ON/OFF valve acts to pass gas each time said output of said flip flop is conductive.

7. The power unit of claim 1 and further including an anesthesia ventilator system and a bellows system having a closed container and a bellows therein wherein the output of said power unit is connected to said closed container and said bellows is connected to said anesthesia ventilator system said power unit compressing the bellows during inspiratory phase time and enabling the bellows to withdraw gas from the patient during the expiratory phase time.

8. A fluid operated bistable oscillator having a fixed phase time ratio of the periods that said oscillator is in each state, said oscillator having input means connected to a fluid source via means for varying the input pressure of said fluid to said oscillator, and display means including graduations calibrated to read respiratory frequency which is responsive to said input pressure, said oscillator including means responsive to said input pressure for controlling the frequency of the change of state of said oscillator in accordance with said input pressure so that said frequency can be controlled and monitored by varying said input pressure and viewing said display means.

9. The oscillator of claim 8 wherein said oscillator has a pneumatic timing circuit for varying the flow of gas to control the frequency of oscillation and said phase time ratio.

10. The oscillator of claim 9 wherein said timing circuit includes a pair of passive timers which include bleed orifices for bleeding off pressure from each of said timers whereby the ratio of said orifices control said phase time ratio.

11. The oscillator of claim 10 wherein said passive timers are utilized in combination witn a fluid flip flop having a supply port and a pair of outputs with each of said passive timers being connected to both of the outputs of said flip flop for controlling the amount of time that each of said outputs of said flip flop are conductive of fluid from the supply port thereof.

12. The oscillator of claim 11 wherein means for connecting each of the passive timers to one of the control inputs of said flip flop is provided for deflecting the flow of fluid from said supply port of said flip flop to the other of said orifices after a predetermined portion of the oscillation cycle of said flip flop.

* * * * *